United States Patent
Kawata et al.

(10) Patent No.: US 9,159,499 B2
(45) Date of Patent: Oct. 13, 2015

(54) ADDITIVES FOR DYE-SENSITIZED SOLAR CELLS

(75) Inventors: Kentaro Kawata, Kanagawa (JP); Tomohisa Goto, Kanagawa (JP); Hiroki Yoshizaki, Tokyo (JP)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/240,922

(22) PCT Filed: Aug. 20, 2012

(86) PCT No.: PCT/EP2012/003532
§ 371 (c)(1),
(2), (4) Date: Feb. 25, 2014

(87) PCT Pub. No.: WO2013/026563
PCT Pub. Date: Feb. 28, 2013

(65) Prior Publication Data
US 2014/0190567 A1    Jul. 10, 2014

(30) Foreign Application Priority Data

Aug. 25, 2011  (EP) ................................. 11006942

(51) Int. Cl.
*C07D 233/56* (2006.01)
*H01G 9/20* (2006.01)
*C09K 9/02* (2006.01)

(52) U.S. Cl.
CPC ............ *H01G 9/2004* (2013.01); *C07D 233/56* (2013.01); *C09K 9/02* (2013.01); *H01G 9/2059* (2013.01); *C09K 2211/1044* (2013.01); *Y02E 10/542* (2013.01)

(58) Field of Classification Search
CPC ........................... H01G 9/2004; C07D 233/56
USPC ............... 548/341.1; 252/62.2; 136/263
See application file for complete search history.

(56) References Cited

U.S. PATENT DOCUMENTS

2012/0135316 A1   5/2012  Resnati et al.

FOREIGN PATENT DOCUMENTS

| EP | 0986079 | A2 | 3/2000 |
| EP | 2261217 | A1 | 12/2010 |
| JP | 2005108664 | A | 4/2005 |
| JP | 2006331995 | A | 12/2006 |
| JP | 2010177197 | A | 8/2010 |
| WO | 2010121900 | A1 | 10/2010 |

OTHER PUBLICATIONS

International Search Report for PCT/EP2012/003532 dated Jan. 7, 2013.
Fei, Z. et al., "A supercooled imidazolium iodide ionic liquid as a low-viscosity electrolyte for dye-sensitized solar cells," Inorg. Chem., 2006, vol. 45, pp. 10407-10409.
Nazeeruddin, M. K. et al., "Conversion of light to electricity by cis-X2Bis(2,2'-bipyridyl-4,4'-dicarboxylate)ruthenium(II) Charge-transfer sensitizers (X=Cl-, Br-, I-, CN-, and SCN-) on Nanocrystalline TiO2 Electrodes," J. Am. Chem. Soc., 1993, vol. 115, pp. 6382-6390.
Kusama, H. et al., "Influence of nitrogen-containing heterocyclic additives in I-/I3- redox electrolytic solution on the performance of Ru-dye-sensitized nanocrystalline TiO2 Solar Cell," Journal of Photochemistry and Photobiology A: Chemistry, 2005, vol. 169, pp. 169-176.
Miyazaki, E. et al., "Synthesis and properties of N'-(3-methoxypropyl)-N3-Methylimidazolium salts," Heterocycles, 2011, vol. 82, No. 2, pp. 1317-1325.
Suryanarayanan, V. et al., "High performance dye-sensitized solar cells containing 1-methyl-3-propyl imidazolinium iodide-effect of additives and solvents," Journal of Electroanalytical Chemistry, 2009, vol. 633, pp. 146-152.
Nat Inst of Adv Ind & Technol, "Photoelective conversion element and dye-sensitized solar cell using above," Espacenet, Publication Date: Apr. 21, 2005; English Abstract of JP-2005 108664.
Sharp KK, "Photoelectric conversion element," Espacenet, Publication Date: Dec. 7, 2006; English Abstract of JP-2006 331995.
Sony Corp, "Method of manufacturing dye-sensitized photoelectric conversion element," Espacenet, Publication Date: Aug. 12, 2010; English Abstract of JP-2010 177197.

*Primary Examiner* — Rebecca Anderson
(74) *Attorney, Agent, or Firm* — Millen, White, Zelano & Branigan, P.C.

(57) ABSTRACT

The present invention relates to the use of at least one imidazol derivative of formula I or 1-(3,3,4,4,4-pentafluorobutyl)-1H-imidazole, 1-(3,3,4,4,4-pentafluorobutyl)-1,2,3-triazole or 1-(2'-thioethyl)ethylimidazole as additive in dye-sensitized solar cells and to special electrolyte formulations and a dye-sensitized solar cell comprising at least one compound of formula I or 1-(3,3,4,4,4-pentafluorobutyl)-1H-imidazole, 1-(3,3,4,4,4-pentafluorobutyl)-1,2,3-triazole or 1-(2'-thioethyl)ethylimidazole.

16 Claims, No Drawings

ADDITIVES FOR DYE-SENSITIZED SOLAR CELLS

The present invention relates to the use of at least one imidazol derivative of formula I or 1-(3,3,4,4,4-pentafluorobutyl)imidazole, 1-(3,3,4,4,4-pentafluorobutyl)1,2,3-triazole or 1-(2'-thioethyl)ethylimidazole as additive in dye-sensitized solar cells and to special electrolyte formulations and a dye-sensitized solar cell comprising at least one compound of formula I or 1-(3,3,4,4,4-pentafluorobutyl)imidazole, 1-(3,3,4,4,4-pentafluorobutyl)-1,2,3-triazole or 1-(2'-thioethyl)ethylimidazole.

Dye-sensitized solar cells utilizing a sensitizer dye have attracted wide attention. Dye-sensitized solar cells include, for example, a transparent conductive film, a porous semiconductor electrode having a sensitizing dye supported therein, a hole transport layer, and a counter electrode formed in this order on a transparent substrate.

An example of such cells is described in literature: O'Regan, B. and Gratzel, M. (1991) *Nature*, 353, 737. The solar cell contains, in this case, a pair of opposite electrodes (an anode and a cathode) and an electrolyte in between them. The electrolyte includes iodide ion couples having different oxidation states as a mediator of holes generated upon charge separation at the dye-sensitized nanoporous semiconductor-electrolyte interface. The cathode is made of a conductive material whilst the anode is made of a plate of transparent materials such as glass having on its surface a transparent conductive layer of light-transmitting tin dioxide ($SnO_2$) which might be doped with another element and also a semiconducting titanium dioxide ($TiO_2$) layer thereon. The $TiO_2$ layer is formed with a $TiO_2$ semiconductor consisting of nanocrystalline particles, to the surface of which sensitizing dyes are attached. When the interface between the $TiO_2$ nanocrystalline layer and dyes is irradiated, electrons are injected to $TiO_2$. On the other hand, the mediator undergoes oxidation within the electrolyte; three iodide ions ($I^-$) eject two electrons, resulting in triiodide ions ($I_3^-$) of high oxidation degree. The electrons are then transported through the $TiO_2$ nanocrystalline layer and collected by the transparent conductive layer whilst the triiodide ions ($I_3^-$) diffuse to the cathode, and obtain two electrons to be reduced into the iodide ions ($I^-$). Thus, this type of wet cell converts solar energy into electric energy.

Dye-sensitized solar cells have been expected to serve as a solar cell for the next generation because of simplicity and convenience of fabrication methods thereof, reduced material costs therefore and the like.

In order for dye-sensitized solar cells to be put in practical use, there has been a demand for further improvement in conversion efficiency, and for that, there has been a demand for an increase in the current to be generated (short-circuit current, $J_{sc}$), in open-circuit voltage ($V_{oc}$) as well as in safety and durability.

The dye-sensitized solar cells that perform best presently contain at least one volatile organic solvent to reduce the viscosity of the electrolyte, thus to enhance the ion mobility. The greatest challenge here is to remove or reduce the volatility of electrolytes by replacing the volatile solvent with ionic liquids with the goal that the electrolyte liquid composes only of ions such as disclosed e.g. in Yu Bai et al., "High-performance dye-sensitized solar cells based on solvent-free electrolytes produced from eutectic melts", *Nature Materials* 2008, 1.

One of the factors that limits the power conversion efficiency of ionic liquid-based DSSC may be the much larger extent of recombination of the injected electron in the semiconductor or conduction band electrons (e.g. $TiO_2$) due to the much larger amount of the oxidized part of the redox couple (e.g. $I_3^-$) at the relevant operating condition. In order to increase the open-circuit voltage, it is necessary to avoid such recombination which means in other words to suppress the leakage current at the semiconductor electrolyte junction.

The leakage current arises e.g. from the described reduction of triiodide by conduction band electrons ($e^-_{cb}$):

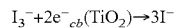
$$I_3^- + 2e^-_{cb}(TiO_2) \rightarrow 3I^-$$

which occurs despite the fact that the $TiO_2$ surface is covered by a monolayer of the dye. The triiodide, due to its relatively small size, either crosses the dye layer or has access to nanometersized pores onto which the dye cannot completely cover, i.e. where the surface of $TiO_2$ is bare and exposed to redox electrolyte.

Typically, recombination is suppressed by addition of compounds which are considered to be coordinated to free sites on the $TiO_2$ surface, thus blocking the access of triiodide or free iodine to potential recombination sites. Examples of compounds typically used for this purpose are (poly)ether derivatives, amides, esters, nitriles. The currently best results have been achieved using N-alkyl-benzimidazoles (Zhaofu Fei et al., *Inorg. Chem.* 2006, 45, 10407-10409, A Supercooled Imidazolium Iodide Ionic Liquid as a Low-Viscosity Electrolyte for Dye-Sensitized Solar Cells), 4-tert-butylpyridine (TBP, M. K. Nazeeruddin et al., *J. Am. Chem. Soc.* 1993, 115, 6382-6390) or nitrogen containing heterocyclic additives such as tetrazole, pyrazole, triazole, pyrazine, pyrimidine, triazine (H. Kusama et al., *J. Photochem. Photobiol., A Chemistry,* 2005, 169-176). TBP and the nitrogen containing heterocyclic additives are described as useful especially in electrolytes comprising at least one volatile organic solvent. It is believed that the donating properties of the nitrogen lone pair in the heterocyclic additives known so far are responsible for the enhanced $V_{oc}$.

An alternative or secondary explanation of the effect is believed that such bases accept protons derived either from the electrolyte or the sensitized electrode so that the acidity of the sensitized electrode surface in the completed device is buffered, ensuring stabilised output over long term testing.

WO 2010/121900 describes the use of N-methylimidazole, N-ethylimidazole and N-propylimidazole as additive for electrolytes in DSSC.

EP 0 986 079 A2 describes heterocycles containing —N=C($R^1$)—, wherein $R^1$ represents an alkyl group, a cycloalkyl group, an aralkyl group, an aryl group, a heterocyclic group, an alkoxy group, an aryloxy group or an acylamino group, as additives for electrolytes in DSSC.

JP 2005-108664 describes a dye-sensitized solar cell comprising an electrolytic solution containing an imidazole compound which may be substituted by an alkyl group, an alkinyl group, a phenyl group, an aminophenyl group, a halogenated phenyl group, an amino group, an aminopropyl group, a cyano group, a cyanomethyl group, a halogen group or a benzyl group, particularly imidazole, 1-(1-butyl)imidazole, 2-ethyl-4-methylimidazole, 5-ethynyl-1-methylimidazole, 1-phenylimidazole, 4-methyl-2-phenylimidazole, 1-(4-aminophenyl)imidazole, 1-(4-fluorophenyl)imidazole, 4-amino-5-cyanoimidazole, 1-(3-aminopropyl)imidazole, 4-cyanomethylimidazole, 4-bromoimidazole, 1-benzyl-2-methylimidazole in solvent based electrolytes using acetonitrile.

JP 2006-331995 describes a dye-sensitized solar cell comprising an electrolytic solution containing an imidazole compound which may be substituted by a hydrocarbon group of 1-12 C atoms, particularly an alkyl group with 1 to 6 C atoms and an aryl group having 6 to 12 C atoms. Solvent based electrolytes containing 2-ethylimidazole, 4-methylimidazole, 2-propylimidazole in acetonitrile, a solid electrolyte containing 2-ethylimidazole and an electrolyte containing ethylmethylimidazolium trifluoromethylsulfonylimide and 2-propylimidazol are described.

JP 2010-177197 describes an additive agent for DSSC containing a phosphonic acid having a long chain alkyl group about 13 C atoms, tert-butylpyridine and 1-methoxybenzimidazole.

However, there continues to be a demand for new and/or improved additives which are able to improve open circuit voltage by shifting the conduction bandedge of oxide semiconductor in a negative direction and/or by reducing the leakage current and therefore maximising the maximum power-operating voltage. The open circuit voltage is one important parameter which needs to be tuned in achieving improved DSC efficiency over a broad temperature range including temperatures above room temperature and well below the temperature at which dye desorption may take place (i.e. in the range of 40° C. to 120° C.)).

The objective of the invention is therefore to provide alternative and/or improved compounds as additives for dye-sensitized solar cells which act as recombination inhibitor and/or as an agent to induce the conduction bandedge shift of the porous semiconductor, preferably to induce that of $TiO_2$.

Surprisingly it was found that special alkoxyalkyl imidazoles or 1-(3,3,4,4,4-pentafluorobutyl)imidazole, 1-(3,3,4,4,4-pentafluorobutyl)-1,2,3-triazole or 1-(2'-thioethyl)ethylimidazole fulfil such demands.

Not being bound by any theory, it is believed that alkoxyalkyl imidazoles of formula I act as recombination inhibitors and/or as agents to induce the conduction bandedge shift of the porous semiconductor resulting in an increase of the open circuit voltage ($V_{oc}$). The alkoxyalkyl imidazoles of formula I or 1-(3,3,4,4,4-pentafluorobutyl)imidazole, 1-(3,3,4,4,4-pentafluorobutyl)-1,2,3-triazole or 1-(2'-thioethyl)ethylimidazole therefore act as additives which are able to reduce the leakage current and to enhance the conduction bandedge, both leading to the increase of $V_{OC}$ as well as maximum power output voltage, $V_{MAX}$.

The present invention therefore relates firstly to the use of at least one compound of formula I

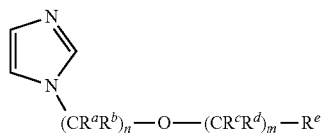

in which
$R^a$, $R^b$, $R^c$, $R^d$ and $R^e$ independently of each other are
H, F, Cl or
straight-chain or branched alkyl with 1 to 20 C atoms which optionally may be partially or fully fluorinated or chlorinated,
n is 1, 2, 3 or 4,
m is 1, 2, 3 or 4,
as additive in dye-sensitized solar cells.

A straight-chain or branched alkyl group having 1 to 20 C atoms is, for example, methyl, ethyl, propyl, isopropyl, n-butyl, sec.-butyl, tert.-butyl, 1-(2,2-dimethyl)-propyl, pentyl, hexyl, heptyl, octyl, x-methylbutyl with x being 1; 2 or 3, x-methylpentyl with x being 1; 2; 3 or 4, x-methylhexyl with x being 1; 2; 3; 4 or 5, x-ethylpentyl with x being 1, 2 or 3, x-ethylhexyl with x being 1; 2; 3 or 4, n-nonyl, n-decyl, n-undecyl, n-dodecyl, n-tridecyl, n-tetradecyl, n-pentadecyl, n-hexadecyl, n-heptadecyl, n-octadecyl, n-nonadecyl and n-eicosyl, which can be partially fluorinated, fully fluorinated, partially chlorinated or fully chlorinated.

The term "fully fluorinated" means that all H atoms are substituted by F atoms in the given alkyl group. The term "partially fluorinated" means that at least one H atom of the given alkyl group is substituted by a F atom. The term "fully chlorinated" means that all H atoms are substituted by Cl atoms in the given alkyl group. The term "partially chlorinated" means that at least one H atom of the given alkyl group is substituted by a Cl atom.

Preferred compounds of formula I, as described above, are compounds in which $R^a$, $R^b$, $R^c$, $R^d$ and $R^e$ are independently of each other H or F.

$R^a$, $R^b$, $R^c$, $R^d$ and $R^e$ are particularly preferably H.

The variable n is preferably 1 or 2.
The variable m is preferably 1 or 2.

Therefore, preferred compounds of formula I are 1-(2-ethoxyethyl)imidazole, 1-(2-methoxyethyl)imidazole, 1-(ethoxymethyl)imidazole and 1-(methoxymethyl)imidazole. 1-(2-ethoxyethyl)imidazole is particularly preferred.

The at least one compound of formula I as described or preferably described above can be used as single additive or in combination with Brønsted or Lewis acidic compounds, for example, a conjugate acid of its own which means a compound of formula Ia

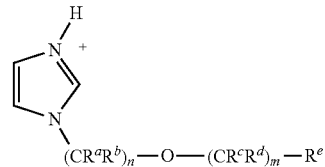

in which $R^a$, $R^b$, n, $R^c$, $R^d$, m and $R^e$ have a meaning as defined above and having a monovalent anion, preferably iodide or thiocyanate,
or a different protonated imidazole compound within said electrolyte. A different protonated imidazole compound is for example an 1-alkoxyalkylimidazolium iodide or an 1-alkylimidazolium iodide. It might also contain other known additives such as (poly)ether derivatives, amides, esters, nitriles or other heterocyclic compounds as mentioned as additives in the prior art.

Compounds of formula Ia can be synthesized through reaction of a compound of formula I together with an acid, preferably HI or a thiocyanate salt capable to protonate the compound of formula I.

The kind of electrolyte useful in the given devices such as the dye-sensitized solar cell is not limited. The electrolytes may be based on molecular solvents or on organic salts, commonly described as molten salts or ionic liquids. It is preferred to use the imidazoles of formula I as described or as preferably described above or 1-(3,3,4,4,4-pentafluorobutyl)imidazole, 1-(3,3,4,4,4-pentafluorobutyl)-1,2,3-triazole or 1-(2'-thioethyl)ethylimidazole in electrolytes which do not contain highly volatile molecules such as low molecular weight organic solvents.

The present invention relates furthermore to an electrolyte formulation comprising at least one compound of formula I as described above or preferably described together with redox active species such as iodide/triiodide or Co(II)/Co(III) complex couples such as Co(II)/Co(III)(dbbip)$_2$ in which dbbip means 2,6-bis(1'-butylbenzimidazol-2'-yl)pyridine, Co(II)/Co(III)(bpy)$_3$ where bpy denotes bipyridine or alkylated bipyridine derivatives thereof, the counter anion being either perchlorate, fluoroperfluoroalkylphosphate such as perfluoroethylpentafluorophosphate, or (fluoro)cyanoborate, particularly tetracyanoborate, preferably a redox couple of iodine and at least one iodide salt as redox active species. This electrolyte formulation shall be used as an electrolyte for a dye sensitized solar cells.

Electrolyte formulations according to the invention comprising the inventive additives of formula I, as described or preferably described above, as alternatives or improvements to already known electrolyte formulations in the field of electrolyte formulations for dye sensitised solar cells. In using the inventive additives, such electrolyte formulations show comparable or increased power conversion efficiencies avoiding disadvantages of currently known additives e.g. tert-butyl-pyridine. The inventive additives of formula I as described or preferably described above increase the open circuit voltage ($V_{oc}$) and thus power conversion efficiency of the dye-sensitized solar cell as defined herein.

In chemistry, an electrolyte is any substance containing free ions that make the substance electrically conductive. The most typical electrolyte is an ionic solution, but molten electrolytes and solid electrolytes are also possible.

An electrolyte formulation according to the invention is therefore an electrically conductive medium, basically due to the presence of at least one substance that is present in a dissolved and or in molten state i.e. supporting an electric conductivity via motion of ionic species. However, the said electric conductivity may not be of the major relevance to the role of the electrolyte of a dye-sensitised solar cell. Therefore, the scope of this invention is not limited to highly conductive electrolyte media.

The term electrolyte may be used for the term electrolyte formulation as well comprising all ingredients as disclosed for the electrolyte formulation.

The total concentration of the compounds of formula I as described or preferably described above is typically in the range from 0.01 to 30 weight % (% w/w) within the electrolyte formulation, preferably from 0.03 to 20 weight %, more preferably 0.1 to 10 weight %.

The electrolyte formulation of the invention comprises preferably iodine (I$_2$). Particularly preferably, it comprises from 0.01 to 30 weight %, more preferably 0.05 to 20 weight % and most preferably from 0.2 to 10 weight % of I$_2$.

The electrolyte formulation of the invention comprises preferably at least one iodide salt.

The iodide salt consists of an inorganic or organic cation and I$^-$ as anion. There exists no limitation to the kind of cation. However, to limit the amount of different cations in the electrolyte formulations, especially for DSC, organic cations shall be used such as organic compounds comprising a quaternary nitrogen atom, preferably cyclic organic cations such as pyridinium, imidazolium, triazolium, pyrrolidinium or morpholinium. Preferably, the electrolyte formulation comprises at least one iodide salt in which the organic cation is independently selected from the group of

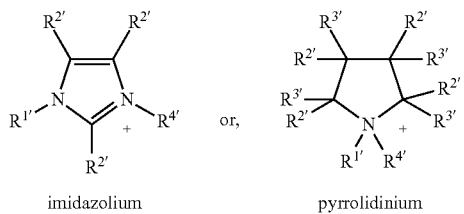

imidazolium            pyrrolidinium in which the substituents
$R^{2'}$ and $R^{3'}$ each, independently of one another, denote H or straight-chain or branched alkyl having 1 to 20 C atoms,
$R^{1'}$ and $R^{4'}$ each, independently of one another, denote straight-chain or branched alkyl having 1-20 C atoms, which optionally may be partially fluorinated or perfluorinated,
straight-chain or branched alkenyl having 2-20 C atoms and one or more double bonds, which optionally may be partially fluorinated,
straight-chain or branched alkynyl having 2-20 C atoms and one or more triple bonds, which optionally may be partially fluorinated.

Particularly preferred examples of the at least one iodide salt are 1-ethyl-3-methylimidazolium iodide (emim I), 1-propyl-3-methylimidazolium iodide (pmim I), 1-butyl-3-methyl-imidazolium iodide (bmim I), 1-hexyl-3-methylimidazolium iodide (hmim I), 1,3-dimethyl-imidazolium iodide (mmim I), 1-allyl-3-methylimidazolium iodide (amim I), N-butyl-N-methyl-pyrrolidinium iodide (bmpl I) or N,N-dimethyl-pyrrolidinium iodide (mmpl I).

Other components of the electrolyte formulation are one or several further salts or solvents or additives as indicated further below.

According to another embodiment of the present invention, the electrolyte formulation comprises at least one further salt with organic cations comprising a quaternary nitrogen and an anion selected from a halide ion, such as F$^-$, Cl$^-$, I$^-$, a polyhalide ion, a fluoroalkanesulfonate, a fluoroalkanecarboxylate, a tri(fluoroalkylsulfonyl)methide, a bis(fluoroalkylsulfonyl)imide, bis(fluorsulfonyl)imide, a nitrate, a hexafluorophosphate, a tris-, bis- and mono-(fluoroalkyl) fluorophosphate, a tetracyanoborate, a dicyanodifluoroborate, a tricyanofluoroborate, a tris-, bis- or monoperfluoroalkylcyanoborate, a bis- or monocyano-perfluoroalkyl-mono- or bis fluoroborate, a perfluoroalkyl-alkoxy-fluorocyanoborate, a perfluoroalkyl-alkoxy-dicyanoborate, a dicyanamide, a tricyanomethide, a mono hydridotricyanoborate, a dihydridodicyanoborate, methyltricyanoborate, ethyltricyanoborate, al lyltricyanoborate, methylethyldicyanoborate, dimethyldicyanoborate, diethyldicyanoborate, a thiocyanate, an alkylsulfonate or an alkylsulfate, with fluoroalkane having 1 to 20 C atoms, preferably perfluorinated, fluoroalkyl having 1 to 20 C atoms and alkyl having 1 to 20 C atoms. Fluoroalkane or fluoroalkyl is preferably perfluorinated.

Preferably, the further salts are selected from salts comprising anions such as thiocyanate, tetracyanoborate, dicyanodifluoroborate, tricyanofluoroborate, a monohydridotricyanoborate, a dihydridodicyanoborate, methyltricyanoborate, ethyltricyanoborate, allyltricyanoborate, methylethyldicyanoborate, dimethyldicyanoborate, diethyldicyanoborate or a combination thereof.

In a preferred embodiment of the invention, the electrolyte formulation according to the invention comprises at least one compound having a tetracyanoborate anion, a dicyanodifluoroborate anion and/or a tricyanofluoroborate anion.

In a preferred embodiment of the invention, the electrolyte formulation according to the invention comprises at least one compound having a mono hydridotricyanoborate, a dihydridodicyanoborate, methyltricyanoborate, ethyltricyanoborate, al lyltricyanoborate, methylethyldicyanoborate, dimethyldicyanoborate or diethyldicyanoborate anion.

The cation of the at least one further salt or of a preferred further salt, preferably having one of the above mentioned anions such as tetracyanoborate, dicyanodifluoroborate anion or tricyanofluoroborate or monohydridotricyanoborate, may be selected amongst inorganic or organic cations, preferably amongst cations comprising a quaternary nitrogen atom, particularly preferably cyclic organic cations such as pyridinium, imidazolium, triazolium, pyrrolidinium or morpholinium.

In another embodiment of the invention,
acids as proton donator, preferably HI,
salts having inorganic cations and a monovalent anion, preferably having an alkali metal cation or an earth alkali metal cation and having iodide, thiocyanate or any other inert anion such as borate anions like tetracyanoborate anions,
salts containing protonated amines such as iodide salts or thiocyanate salts of imidazolium, 1-substituted imidazolium, benzimidazolium or 1-substituted benzimidazolium which are independently of each other substituted by a straight-chain or branched alkyl having 1 to 4 C atoms which may be non-fluorinated, partially fluorinated or perfluorinated, a straight-chain or branched alkoxyalkyl having 1 to 8 C atoms or a cycloalkyl having 3 to 7 C atoms
or a guanidinium salt, preferably guanidinium iodide or guanidinium thiocyanate may be added to the electrolyte formulation comprising at least one additive according to the invention.

In a preferred embodiment of the invention iodide or thiocyanate salts are added having an inorganic cation, preferably an alkali metal cation or an earth alkali metal cation, a guanidinium cation or a cation being a protonated amine, preferably imidazolium, benzimidazolium or 1-substituted imidazolium or 1-substituted benzimidazolium in which the substitution is independently of each other selected from a straight-chain or branched alkyl having 1 to 4 C atoms which may be non-fluorinated, partially fluorinated or perfluorinated, a straight-chain or branched alkoxyalkyl having 1 to 8 C atoms or a cycloalkyl having 3 to 7 C atoms Preferred inorganic salts are lithium iodide, lithium thiocyanate, magnesium iodide or magnesium thiocyanate.

Preferred guanidinium salts are guanidinium iodide or guanidinium thiocyanate.

Preferred salts having a cation being a protonated amine are imidazolium iodide, imidazolium thiocyanate, benzimidazolium iodide, benzimidazolium thiocyanate, 1-ethylimidazolium iodide, 1-ethylimidazolium thiocyanate, 1-butylimidazolium iodide or 1-butylimidazolium thiocyanate.

In one embodiment of the invention, an electrolyte formulation is preferred comprising at least one salt having an iodide or a thiocyanate anion and its cation is a protonated amine.

The following combinations of iodide salts and a further compound and/or additive are preferred:
a) mmim I and emimTCB (1-ethyl-3-methylimidazolium tetracyanoborate)
b) pmim I (1-propyl-3-methylimidazolium iodide) and emim TCB
c) mmim I, amim I and emimTCB
d) mmim I, emim I and emim TCB
e) mmim I, guanidinium iodide and emim TCB
f) mmim I, guanidinium thiocyanate and emim TCB
g) mmim I, lithium iodide and emim TCB
h) mmim I, lithium thiocyanate and emim TCB
i) mmim I, magnesium iodide and emim TCB.
j) mmim I, magnesium thiocyanate and emim TCB.
k) mmim I, imidazolium iodide and emimTCB
l) mmim I, imidazolium thiocyanate and emimTCB
m) mmim I, imidazolium iodide, emim thiocyanate and emimTCB
n) mmim I, benzimidazolium iodide and emimTCB
o) mmim I, benzimidazolium thiocyanate and emimTCB
p) mmim 1,1-ethylimidazolium thiocyanate and emimTCB
q) mmim 1,1-ethylimidazolium iodide and emimTCB
r) mmim 1,1-butylimidazolium iodide and emimTCB
s) mmim 1,1-butylimidazolium thiocyanate and emimTCB
t) mmimI and emim MFB (1-ethyl-3-methylimidazolium fluorotricyanoborate)
u) mmimI and emim DDB (1-ethyl-3-methylimidazolium dicyanodifluoroborate)
v) mmim I and emim MHB (1-ethyl-3-methylimidazolium monohydridotricyanoborate).

emim means 1-ethyl-3-methylimidazolium.
pmim means 1-propyl-3-methylimidazolium
mmim means 1,3-dimethylimidazolium
amim means 1-allyl-3-methylimidazolium The electrolyte formulation of the present invention may further comprise at least one compound containing a nitrogen atom having non-shared electron pairs as additional additive beside of the inventive compounds of formula I, as described or preferably described before, or tert.-butyl-pyridine. Examples of such compounds are found in EP 0 986 079 A2, starting on page 2, lines 40-55, and again from page 3, lines 14 extending to page 7, line 54, which are expressly incorporated herein by reference.

The following compounds are also useful as additives in opto-electronic devices, preferably in dye-sensitized solar cells:
1-(2-methoxyethoxymethyl)-1H-imidazole,
1-(3,3,4,4,4-pentafluorobutyl)-1H-imidazole,
1-(3,3,4,4,4-pentafluorobutyl)-1,2,4-triazole,
1-(3,3,4,4,4-pentafluorobutyl)-1,2,3-triazole,
N-(3,3,4,4,4-pentafluorobutyl)-benzimidazole,
3-imidazol-1-yl-propylamine,
1-(2'-thioethyl)ethyl-imidazole,
1-n-pentyl-1H-imidazole,
1-n-hexyl-1H-imidazole,
1-n-heptyl-1H-imidazole,
1-n-octyl-1H-imidazole,
1-n-nonyl-1H-imidazole,
1-n-decyl-1H-imidazole,
1-cyclopropyl-1H-imidazole,
1-(cyclopentyl)-1H-imidazole,
1-(cyclohexyl)-1H-imidazole,
1-(cycloheptyl)-1H-imidazole,
1-(cyclooctyl)-1H-imidazole,
1-(1-adamantyl)-1H-imidazole,
1-(2-adamantyl)-1H-imidazole,
1-isopropyl-1H-imidazole,
1-(2-methylpropyl)-1H-imidazole,
1-(3-methylbutyl)-1H-imidazole,
1-(1,1-dimethylethyl)-1H-imidazole,
1-(2-ethylhexyl)-1H-imidazole,
1-(3,7-dimethyloctyl)-1H-imidazole,
1-(2,2,2-trifluoromethyl)ethyl-1H-imidazole
1-(3-propylheptyl)-1H-imidazole,
2-methyl-1H-imidazole, 4,5-dimethyl-1H-imidazole,
4,5-dicyano-1H-imidazole,
2-methyl-4-nitro-1H-imidazole,
4-nitro-1H-imidazole,
1-methyl-2-mercaptoimidazole,
2-phenyl-imidazole,
4-phenyl-imidazole,
1-(trimethylsilylmethyl)-1H-imidazole,
1-(2-cyanoethyl)-1H-imidazole,
1H-imidazole-4,5-dicarboxylic acid,
1-(n-butyl)-4,5-dimethyl-1H-imidazole,
trans-1,2-Cyclohexyl-bis-1',1"-imidazole
2-methyl-1H-benzimidazole,
2-hydroxy-1H-benzimidazole,
5,6-dimethyl-1H-benzimidazole,
5-nitro-1H-benzimidazole,
1-(4-methoxyphenyl)-1H-imidazole,
1-(4-cyanophenyl)-1H-imidazole,
1-(2,3,4,5,6-pentafluorophenyl)-1H-imidazole,
1-(2-methoxyethyl)benzimidazole,
1-(1-methoxyethoxy)methylbenzimidazole,
1-(2-ethoxyethyl)benzimidazole
1-butyl-1H-benzotriazole,
1-(2-methoxy-ethyl)-1H-benzotriazole,
9-butyl-9H-purine,
1-n-butyl-6-azaindole,
1-(2-methoxyethyl)-6-azaindole,
9-(2-methoxyethyl)-9H-purine,
4,5,6,7-tetrahydro-1H-benzimidazole,
1-butyl-4,5,6,7-tetrahydro-1H-benzimidazole,
4,5,6,7-tetrahydro-1H-benzotriazole,
1-butyl-4,5,6,7-tetrahydro-1H-benzotriazole,
1,2-bis(1-ethoxyimidazole)ethane
1-(2',2',6',6'-tetramethylpiperizino)imidazole
1,4-di-(1-imidazole)butane,
di-(1-imidazole)methane,
di-(1-imidazolemethyl)sulfide,
1-methoxyethoxymethylbenzimidazole,
1-methoxyethylindazole,
1-n-butylpyrazole,
1-(2-methoxyethyl)pyrazole.
1-(2-ethoxyethyl)pyrazole
1-(2-ethoxyethyl)-1,2,3-triazole
1-(2-ethoxyethyl)-1,2,4-triazole,
1-n-butylindazole,
2,2'-biimidazole,
4,4',5,5'-tetramethyl-2,2'-biimidazole.

As can be shown in Example C and D below, the additive 1-(3,3,4,4,4-pentafluorobutyl)-1H-imidazole and the additive 1-(3,3,4,4,4-pentafluorobutyl)-1,2,3-triazole give a higher efficiency compared to NBB.

The present invention therefore relates in another aspect of the invention to the use of 1-(3,3,4,4,4-pentafluorobutyl)-1H-imidazole or 1-(3,3,4,4,4-pentafluorobutyl)-1,2,3-triazole as additive in dye-sensitized solar cells.

The present invention therefore relates to an electrolyte formulation comprising at least 1-(3,3,4,4,4-pentafluorobutyl)-1H-imidazole or 1-(3,3,4,4,4-pentafluorobutyl)-1,2,3-triazole together with redox active species.

As can be shown in Example B, the additive 1-(2'-thioethyl)ethylimidazole give a unexpected high efficiency.

The present invention therefore relates in another aspect of the invention to the use of 1-(2'-thioethyl)ethylimidazole as additive in dye-sensitized solar cells.

The present invention therefore relates to an electrolyte formulation comprising at least 1-(2'-thioethyl)ethylimidazole together with redox active species.

The explanations to electrolyte formulations comprising at least one compound of formula I as described or preferably described before on page 7, line 15 to page 15, line 5 are also binding for the electrolyte formulations comprising 1-(3,3,4,4,4-pentafluorobutyl)imidazole, 1-(3,3,4,4,4-pentafluorobutyl)-1,2,3-triazole or 1-(2'-thioethyl)ethylimidazole.

The electrolyte formulation of the present invention may comprise an organic solvent. Preferably, the inventive electrolyte formulation comprises less than 50% of an organic solvent. Particularly preferably, the electrolyte formulation comprises less than 40%, more preferably less than 30%, still more preferably less than 20% and even less than 10%. Most preferably, the electrolyte formulation comprises less than 5% of an organic solvent. For example, it is substantially free of an organic solvent. Percentages are indicated on the basis of weight %.

Organic solvents, if present in such amounts as indicated above, may be selected from those disclosed in the literature. Preferably, the solvent, if present, has a boiling point higher than 160 degrees centigrade, more preferably higher than 190 degrees such as propylene carbonate, ethylene carbonate, butylene carbonate, γ-butyrolactone, γ-valerolactone, glutaronitrile, adiponitrile, N-methyloxazolidinone, N-methylpyrrolidinone, N,N'-dimethylimidazolidinone, N,N-dimethylacetamide, cyclic ureas preferably 1,3-dimethyl-2-imidazolidinone or 1,3-dimethyl-3,4,5,6-tetrahydro-2(1H)-pyrimidinone, glymes preferably tetraglyme, sulfolane, sulfones which are preferably asymmetrically substituted such as 2-ethanesulfonyl-propane, 1-ethanesulfonyl-2-methyl-propane or 2-(propane-2-sulfonyl)-butane, 3-methylsulfolane, dimethylsulfoxide, trimethylphosphate and methoxy-substituted nitriles. Other useful solvents are acetonitrile, benzonitrile and or valeronitrile.

If a solvent is present in the electrolyte formulation, there may further be comprised a polymer as gelling agent, wherein the polymer is polyvinylidenefluoride, polyvinylidene-hexafluoropropylene, polyvinylidene-hexafluoropropylene-chlorotrifluoroethylene copolymers, nafion, polyethylene oxide, polymethylmethacrylate, polyacrylonitrile, polypropylene, polystyrene, polybutadiene, polyethyleneglycol, polyvinylpyrrolidone, polyaniline, polypyrrole, polythiophene. The purpose of adding these polymers to electrolyte formulations is to make liquid electrolytes into quasi-solid or solid electrolytes, thus improving solvent retention, especially during aging.

The electrolyte formulation of the invention may further comprise metal oxide nanoparticles like $SiO_2$, $TiO_2$, $Al_2O_3$, MgO or ZnO, for example, which are also capable of increasing solidity and thus solvent retention.

The present invention therefore relates further to the use of the electrolyte formulation as described in detail above in a dye-sensitized solar cell.

The present invention therefore relates furthermore to a dye-sensitized solar cell comprising at least one compound of formula I as described or preferably described herein.

One preferred embodiment of the invention is the dye-sensitized solar cell as described above in which the at least one compound of formula I is contained in the electrolytic solution or with other words in which the at least one compound of formula I is part of the electrolytic formulation.

In dye-sensitized solar cells, a dye is used to absorb the sunlight to convert into the electrical energy. There are no restrictions per se with respect to the choice of the dye as long as the LUMO energy state is marginally above the conduction bandedge of the photoelectrode to be sensitized. Examples of dyes are disclosed in EP 0 986 079 A2, EP 1 180 774 A2 or EP 1 507 307 A1.

Preferred dyes are organic dyes such as MK-1, MK-2 or MK-3 (its structures are described in FIG. 1 of N. Koumura et al, J. Am. Chem. Soc. Vol 128, no. 44, 2006, 14256-14257), D102 (CAS no. 652145-28-3), D-149 (CAS no. 786643-20-7), D205 (CAS no. 936336-21-9), D358 (CAS no. 1207638-53-6) YD-2 as described in T. Bessho et al, Angew. Chem. Int. Ed. Vol 49, 37, 6646-6649, 2010, Y123 (CAS no. 1312465-92-1), bipyridin-Ruthenium dyes such as N3 (CAS no. 141460-19-7), N719 (CAS no. 207347-46-4), Z907 (CAS no. 502693-09-6), C101 (CAS no. 1048964-93-7), C106 (CAS no. 1152310-69-4), K19 (CAS no. 847665-45-6), SK-1 (CAS no. 906061-30-1) or terpyridine-Ruthenium dyes such as N749 (CAS no. 359415-47-7).

Particularly preferred dyes are Z907 or Z907Na which are both an amphiphilic ruthenium sensitizer or D205. The dye Z907Na means NaRu(2,2'-bipyridine-4-carboxylic acid-4'-carboxylate)(4,4'-dinonyl-2,2'-bipyridine)(NCS)$_2$.

The structure of D205 is

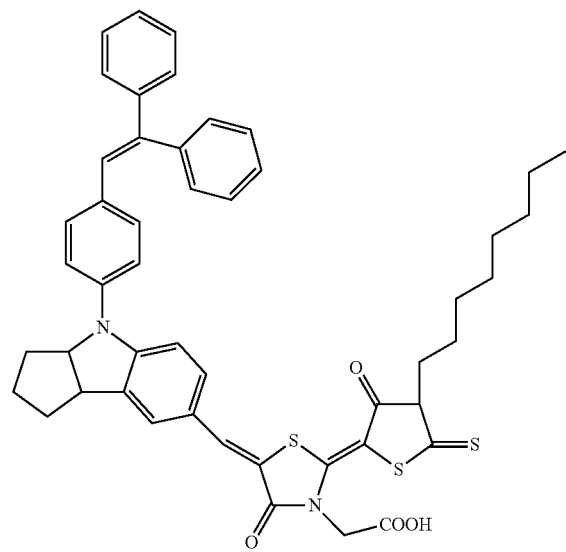

Very particularly preferred dyes are Z907 or Z907Na.

In a preferred embodiment, the dye is coadsorbed with a phosphinic acid. A preferred example of a phosphinic acid is bis(3,3-dimethyl-butyl)-phosphinic acid (DINHOP) as disclosed in M. Wang et al, Dalton Trans., 2009, 10015-10020.

For example, a dye-sensitized solar cell comprises a photoelectrode, a counter electrode and, between the photoelectrode and the counterelectrode, an electrolyte formulation or a charge transporting material, and wherein a sensitizing dye is absorbed on the surface of the photoelectrode, on the side facing the counterelectrode.

According to a preferred embodiment of the device according to the invention, it comprises a semiconductor, the electrolyte formulation as described above and a counter electrode.

According to a preferred embodiment of the invention, the semiconductor is based on material selected from the group of Si, TiO$_2$, SnO$_2$, Fe$_2$O$_3$, WO$_3$, ZnO, Nb$_2$O$_5$, CdS, ZnS, PbS, Bi$_2$S$_3$, CdSe, GaP, InP, GaAs, CdTe, CuInS$_2$, and/or CuInSe$_2$. Preferably, the semiconductor comprises a mesoporous surface, thus increasing the surface optionally covered by a dye and being in contact with the electrolyte. Preferably, the semiconductor is present on a glass support or plastic or metal foil. Preferably, the support is conductive.

The device of the present invention preferably comprises a counter electrode. For example, fluorine doped tin oxide or tin doped indium oxide on glass (FTO- or ITO-glass, respectively) coated with Pt, carbon of preferably conductive allotropes, polyaniline or poly(3,4-ethylenedioxythiophene) (PEDOT). Metal substrates such as stainless steel or titanium sheet may be possible substrates beside glass.

The device of the present invention may be manufactured as the corresponding device of the prior art by simply replacing the electrolyte by the electrolyte formulation of the present invention. For example, in the case of dye-sensitized solar cells, device assembly is disclosed in numerous patent literature, for example WO 91/16719 (examples 34 and 35), but also scientific literature, for example in Barbé, C. J., Arendse, F., Comte, P., Jirousek, M., Lenzmann, F., Shklover, V., Grätzel, M. J. Am. Ceram. Soc. 1997, 80, 3157; and Wang, P., Zakeeruddin, S. M., Comte, P., Charvet, R., Humphry-Baker, R., Grätzel, M. J. Phys. Chem. B 2003, 107, 14336.

Preferably, the sensitized semiconducting material serves as a photoanode. Preferably, the counter electrode is a cathode.

The present invention provides a method for preparing a photoelectric cell comprising the step of bringing the electrolyte formulation of the invention in contact with a surface of a semiconductor, said surface optionally being coated with a sensitizer. Preferably, the semiconductor is selected from the materials given above, and the sensitizer is preferably selected from quantum dots and/or a dye as disclosed above, particularly preferably selected from a dye.

Preferably, the electrolyte formulation may simply be pured on the semiconductor or it may be applied to the otherwise completed device already comprising a counter electrode by creating a vacuum in the internal lumen of the cell through a hole in the counter electrode and adding the electrolyte formulation as disclosed in the reference of Wang et al., J. Phys. Chem. B 2003, 107, 14336.

The compounds of formula I, as described above, are commercially available or may be synthesized by already known methods.

To obtain many class of the functional materials for various applications, the substitution of a N atom of a heteroaromatic with halogenated substances to form a carbon-nitrogen bond is widely developed. These heteroaromatics are used as one of the most important key materials for drug discovery, organo-electronics fields development (e.g., organic photovoltaic, organic light emitting diode, organic semiconductor devices).

In general the substitution needs a combination of a strong base (e.g., KH, NaH, LiOH, KOH, NaOH), sometimes of a phase-transfer catalyst (e.g., tetraalkylammonium salt, crown ether), an organic-aqueous bi-phase reaction, reactive leaving groups (e.g., iodine or bromine) of the electrophile, high reaction temperatures and long reaction times with excess amount of substrate (*J. Org. Chem.*, 1954, 19, 1428; *J. Am. Chem. Soc.*, 1984, 106, 6379; *Tetrahedron Lett.*, 1979, 20, 4709-4712; *Heterocycles*, 1984, 38, 4, 793-802; *Tetrahedron*, 2004, 60, 5807-5825; *Tetrahedron Lett.*, 2006, 47, 1575-1579; *Adv. Mater.*, 2007, 19, 1133-1137; *Polyhedron*, 2008, 27, 87-94; *J. Am. Chem. Soc.*, 2008, 130, 12590-12591).

However, under such strong basic condition at high temperature, undesired reaction course(s), e.g., quarternalization of nitrogen, nucleophilic carbon-carbon bond formation also proceeds simultaneously, for example, in case of alkylation of benzimidazole as figured in Eq. 2:

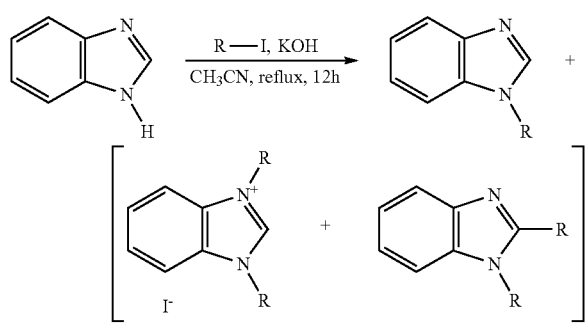

Further, in workup procedure, difficultly removable (viscous, or bulky) salts or polymerized side products prevent from smooth extraction, separation or filtration process.

To solve the above mentioned problems for the synthesis of the compounds of formula I, as described above, for use in dye-sensitzized solar cells, microwave is irradiated to the reaction mixture to give uniform heat, in short time (within 20 min.). The reaction mixture consists of equal equivalent of alkylhalide to substituted nitrogen numbers in the starting material, solvent, and the base. The base, e.g. $K_2CO_3$ particles, replace alkali metal hydrides and alkali metal hydroxides, with easy operation and safety.

After short-time reaction with microwave irradiation, only three (3)-step workup is carried out to obtain the desired product easily:

Step 1) the settled base and the salt in the reaction mixture are filtered off,

Step 2) the solvent is evaporated from filtered solution under reduced pressure, Step 3) the substituted product is purified by column chromatography, distillation, or recrystallization.

According to this improved manner of N-alkylation and N-alkoxyalkylation, N-substituted heteroaromatics of formula I are prepared in high yield.

Halogenated compounds shall be used as alkylation reagent such as iodide, bromide or chloride.

Solvents shall be used such as aprotic, high-polar, and medium-high boiling point organic media, e.g. DMF (N,N-dimethylformamide), DMSO (dimethylsulfoxide), DMI (1,3-dimethyl-2-imidazolidinone), DBU (diazabicycloundecene), preferably DMF.

Typical molar concentrations of the microwave reaction are in the range from 0.01 to 1 molar (mol/L) in the solvent, preferably from 0.05 to 1 molar, more preferably 0.1 to 0.5 molar.

Inorganic or organic bases shall be used within the described microwave assisted reaction such as inorganic carbonates like ammonium carbonate, lithium carbonate, potassium carbonate, sodium carbonate, calcium carbonate, barium carbonate, magnesium carbonate, caesium carbonate, silver carbonate or copper carbonate.

Typical amounts of the base are in the range from 1.1 to 3 equivalent per 1 equivalent of the leaving group of the electrophile, preferably from 1.5 to 3 molar, more preferably 2 to 2.5 equivalent.

The electric power of the microwave is in the range from 200 to 400 W, preferably from 250 to 300 W.

The reaction temperature is in the range from 100 to 180° C., preferably from 120 to 140° C.

The reaction time is consequently in the range from 1 to 30 minutes, preferably from 3 to 20 minutes.

Even without further comments, it is assumed that a person skilled in the art will be able to utilise the above description in the broadest scope. The preferred embodiments and examples should therefore merely be regarded as descriptive disclosure which is absolutely not limiting in any way.

The synthesized compounds are characterized through NMR spectroscopy or elemental analysis. The NMR spectrum is measured in $CDCl_3$. Used frequencies: $^1H$, 399.78 MHz and $^{13}C$, 100.52 MHz, external references: TMS for $^1H$ and $^{13}C$. $^1H$ and $^{13}C$ NMR spectra were recorded on a JEOL JNM-LA3000 spectrometer. All spectra were recorded at ambient temperatures.

Melting point experiments were performed on METTLER TOLEDO FP90 Central Processor and FP81 HT MBC Cell.

EXAMPLE 1

Synthesis of N-Alkoxyalkyl Imidazoles

To a solution of imidazole, 2.0-3.0 equivalent of base is added and mixed with them stirring vigorously. Then dropwise, a solution of 1 equivalent of the alkoxyalkylhalide dissolved in a solvent is added and the mixture is irradiated in a microwave oven placed under a hood operating at 200-400 W power for 3-20 min. The solid of base in the reaction mixture is filtered off after cooling to room temperature, then the solvent is evaporated under reduced pressure. The concentrated residue is purified by distillation or recrystallization after silica gel short column chromatography.

This general procedure applies additionally for the N-alkylation of other azoles such as imidazoles or benzimidazoles.

The following compounds are synthesized according to the above mentioned process.

1-(2-Methoxyethyl)-1H-imidazole in a yield of 92%.

$^1H$ NMR (400 MHz, $CDCl_3$) δ (ppm) 2.01 (quint, J=5.4 Hz, 2H), 3.30 (t, J=5.4 Hz, 2H), 3.33 (s, 3H), 4.06 (t, J=6.8 Hz, 2H), 6.91 (t, J=1.3 Hz, 1H), 7.05 (s, 1H), 7.47 (s, 1H).

$^{13}C$ NMR (100 MHz, $CDCl_3$) δ (ppm) 30.9, 43.5, 58.6, 68.2, 118.9, 129.0, 137.1.

1-(2-Ethoxyethyl)-1H-imidazole in a yield of 76%.

$^1H$ NMR (400 MHz, $CDCl_3$) δ (ppm) 1.11 (t, J=5.2 Hz, 3H), 3.41 (quint. J=5.2 Hz, 2H), 3.85 (t, J=5.2 Hz, 2H), 3.90 (t, J=6.7 Hz, 2H), 6.87 (s, 1H), 7.04 (s, 1H), 7.42 (s, 1H)

$^{13}C$ NMR (100 MHz, $CDCl_3$) δ (ppm) 15.2, 52.3, 67.3, 71.6, 120.3, 122.6, 138.1

EXAMPLE A

The following electrolyte formulations are synthesized to demonstrate the application of electrolyte formulations according to the invention containing emim TCB in dye sensitized solar cells.

The following electrolyte formulation is used:

$I_2$ 2.5%, mmimI 43.4%, guaSCN 0.7%, emimTCB 50.4%, additive as described in detail below 3% in w/w.

The electrolyte formulations are prepared through mixing of 1,3-dimethylimidazolium iodide (mmimI), 1-methyl-3-ethylimidazolium tetracyanoborate (emimTCB), iodine and guanidiniumthiocyanate. It may be necessary to apply heat up to 60° C. to make the electrolyte formulation homogeneous.

The compounds mmimI, emimI, $I_2$, and emimTCB are commercially available or may be synthesized based on known literature such as Bonhote, P et al. *Inorg. Chem.* 1996, 35, 1168-1178 or such as WO 2004/072089 for the synthesis of organic salts with tetracyanoborate anions.

The following additives are used in the above described electrolyte formulation:

| Electrolyte 1 | 1-(2-ethoxyethyl)-1H-imidazole |
| Electrolyte 2 | 1-(2-methoxyethyl)-1H-imidazole |
| Electrolyte 3 | 1-(methoxymethyl)-1H-imidazole |
| Electrolyte 4 | 1-(ethoxymethyl)-1H-imidazole |
| In comparison to | |
| Electrolyte 5 | imidazole |
| Electrolyte 6 | 1-methyl-1H-imidazole |
| Electrolyte 7 | 1-(n-butyl)-1H-imidazole. |

The dye sensitized solar cells are fabricated as disclosed in U.S. Pat. No. 5,728,487 or WO 2007/093961:

A double-layer, mesoporous $TiO_2$ electrode is prepared as disclosed in Wang P. et al., *J. Phys. Chem. B* 2003, 107, 14336, in particular page 14337, in order to obtain a photoanode consisting of a double layer structure. To prepare a transparent nanoporous $TiO_2$ electrode, a screen printing paste containing terpineol solvent and nanoparticulate $TiO_2$ of anatase phase with 20-30 nm diameter was deposited on a transparent conductive substrate to 5 mm×5 mm squared shape by using a hand printer. The paste was dried for 10 minutes at 120 degrees Celsius. Another screen printing paste containing $TiO_2$ with 400 nm diameter was then deposited on top of the nanoporous layer to prepare an opaque layer. The double layer film was then sintered at 500 degrees Celsius for an hour with the result of an underlying transparent layer (7 microns thick) and a top opaque layer (4 microns thick). After sintering, the electrode was immersed in 40 mM aqueous solution of $TiCl_4$ (Merck) for 30 minutes at 70 degrees Celsius and then rinsed quickly with pure water sufficiently. Thus $TiCl_4$-treated electrode was dried at 500 degrees Celsius for 30 minutes just before dye sensitization. The electrode was dipped into a 0.3 mM Z907 dye solution of acetonitrile (Merck HPLC grade) and tert-butyl alcohol (Merck), v:v=1:1 for 60 hours at 19 degrees Celsius. The counter electrode was prepared with thermal pyrolysis method as disclosed in the reference above. A droplet of 5 mM solution of platinic acid (Merck) was casted at 8 μl/cm2 and dried on a conductive substrate. The dye sensitized solar cell was assembled by using 30 micron thick Bynel (DuPont, USA) hot-melt film to seal up by heating. The internal space was filled with each of the electrolyte formulations as described herein to produce the corresponding devices.

The dye Z907 is an amphiphilic ruthenium sensitizer Ru(2, 2'-bipyridine 4,4'-dicarboxylic acid) (4,4'-dinonyl-2,2'-bipyridine)$(NCS)_2$ or $[Ru(H2dcbpy)(dnbpy)(NCS)_2]$.

In order to obtain accurate light intensity level, Air Mass 1.5 Global (AM1.5G) simulated sunlight was calibrated spectrally according to Seigo Ito et al. "Calibration of solar simulator for evaluation of dye-sensitized solar cells" Solar Energy Materials & Solar Cells 82 (2004) 421.

The measurements of photocurrent-voltage curves are carried out for devices placed on a black plate chilled down to 25° C. under 1 Sun illumination. A photomask of 4 mm×4 mm is placed on top of the fabricated devices to define the light projection area.

Energy conversion efficiency is generally the ratio between the useful output of an energy conversion machine and the input of light radiation, in energy terms, determined by using adjustable resistant load to optimize the electric power output.

Thus obtained photovoltaic parameters are summarized in Table 1:

| Electrolyte | $J_{SC}$ [mAcm$^{-2}$] | $V_{OC}$ [V] | FF | η [%] |
|---|---|---|---|---|
| 1 | 10.58 | 0.0.74 | 0.73 | 5.8 |
| 2 | 10.19 | 0.77 | 0.75 | 5.8 |
| 3 | 10.39 | 0.73 | 0.74 | 5.6 |
| 4 | 10.66 | 0.73 | 0.72 | 5.6 |
| 5* | 8.63 | 0.77 | 0.70 | 4.8 |
| 6* | 9.11 | 0.75 | 0.79 | 5.3 |
| 7* | 10.23 | 0.74 | 0.73 | 5.5 |

*not according to the invention
$J_{SC}$ = short circuit current
$V_{OC}$ = open circuit voltage
FF = fill factor
η = power conversion efficiency Within these measurements, Alkoxyalkyl imidazoles give a higher efficiency than the additives N-butylimidazole, N-methylimidaole or imidazole.

EXAMPLE B

The following electrolyte formulations are synthesized to demonstrate the application of electrolyte formulations according to the invention containing 1-butyl-1-methylimidazolium monomethylcyanoborate in dye sensitized solar cells.

The dye sensitized solar cells are fabricated according to Example A and the measurements were done according to Example A.

The electrolyte formulations are prepared through mixing of one or more of 1,3-dimethylimidazolium iodide (mmimI), iodine, the additive as listed below, 1-butyl-1-methylimidazolium monomethylcyanoborate and guanidinium thiocyanate (guaSCN) in weight % as listed below.

| Electrolyte 8 | weight % |
|---|---|
| $I_2$ | 1.3 |
| mmim I | 35 |
| guaSCN | 0.7 |
| 1-(2-ethoxyethyl)-1H-imidazole | 3.0 |
| bmim monomethylcyanoborate | 60 |
| total | 100 |

| Electrolyte 9 | |
|---|---|
| $I_2$ | 1.3 |
| mmim I | 35 |
| guaSCN | 0.7 |
| 1-(3,3,4,4,4-pentafluorobutyl)-1H-imidazole | 3.0 |
| bmim monomethylcyanoborate | 60 |
| total | 100 |

| Electrolyte 10 | |
|---|---|
| $I_2$ | 1.3 |
| mmim I | 35 |
| guaSCN | 0.7 |
| 1-(2'-thioethyl)ethyl-imidazole | 3.0 |
| bmim monomethylcyanoborate | 60 |
| total | 100 |

Thus obtained photovoltaic parameters are summarized in Table 2:

| Electrolyte | $J_{SC}$ [mAcm$^{-2}$] | $V_{OC}$ [V] | FF | η [%] |
|---|---|---|---|---|
| 8 | 9.96 | 0.78 | 0.65 | 5.0 |
| 9 | 9.66 | 0.79 | 0.61 | 4.6 |
| 10 | 10.98 | 0.76 | 0.73 | 6.2 |

$J_{SC}$ = short circuit current
$V_{OC}$ = open circuit voltage
FF = fill factor
η = power conversion efficiency

EXAMPLE C

The following electrolyte formulations are synthesized to demonstrate the application of electrolyte formulations according to the invention relative to an electrolyte formulation with N-butylbenzimidazole containing 1-ethyl-1-methylimidazolium monohydridotricyanoborate in dye sensitized solar cells.

The dye sensitized solar cells are fabricated according to Example A and the measurements were done according to Example A.

The dye sensitized solar cells are fabricated and measured as disclosed in Example A with Z907 and analogously with the dye C106/DINHOP and with the dye SK-1.

For the dye C106, the electrode was dipped into a dye solution being 0.3 mM for the dye C106 and 0.075 mM for DINHOP (solvent mixture acetonitrile (Merck HPLC grade) and tert-butyl alcohol (Merck), v:v=1:1) for 64 hours at 6 degrees Celsius.

For the dye SK-1, the electrode was prepared according to Example A.

The electrolyte formulations are prepared through mixing of the below listed components in weight %.

| Electrolyte 11* | weight % |
|---|---|
| I$_2$ | 1.45 |
| mmim I | 35.54 |
| guaSCN | 0.68 |
| emim monohydridotricyanoborate | 59.22 |
| NBB | 3.11 |
| total | 100 |

| Electrolyte 12 | weight % |
|---|---|
| I$_2$ | 1.47 |
| mmim I | 35.85 |
| guaSCN | 0.68 |
| 1-(2-methoxyethyl)-1H-imidazole | 2.25 |
| emim monohydridotricyanoborate | 59.75 |
| total | 100 |

| Electrolyte 13 | |
|---|---|
| I$_2$ | 1.47 |
| mmim I | 35.94 |
| guaSCN | 0.69 |
| 1-methoxymethyl-1H-imidazole | 2.0 |
| emim monohydridotricyanoborate | 59.9 |
| total | 100 |

| Electrolyte 14 | |
|---|---|
| I$_2$ | 1.44 |
| mmim I | 35.27 |
| guaSCN | 0.67 |
| 1-(3,3,4,4,4-pentafluorobutyl)-1H-imidazole | 3.82 |
| emim monohydridotricyanoborate | 58.79 |
| total | 100 |

Table 3 summarizes the results of the measurements of the above cited electrolyte formulations 11 to 14:

| Electrolyte | $J_{SC}$ [mAcm$^{-2}$] | $V_{OC}$ [V] | FF | η [%] |
|---|---|---|---|---|
| Z907 | | | | |
| 11* | 11.28 | 0.74 | 0.72 | 5.94 |
| 12 | 10.48 | 0.76 | 0.75 | 5.97 |
| 13 | 11.15 | 0.75 | 0.74 | 6.20 |
| 14 | 12.08 | 0.74 | 0.70 | 6.65 |
| C106 | | | | |
| 11* | 11.42 | 0.75 | 0.77 | 6.59 |
| 12 | 10.93 | 0.75 | 0.73 | 5.94 |
| 13 | 10.61 | 0.73 | 0.78 | 6.07 |
| 14 | 10.87 | 0.77 | 0.77 | 6.46 |
| SK-1 | | | | |
| 11* | 12.20 | 0.68 | 0.75 | 6.24 |
| 12 | 11.03 | 0.69 | 0.73 | 5.54 |
| 13 | 11.41 | 0.67 | 0.74 | 5.63 |
| 14 | 11.87 | 0.69 | 0.72 | 5.92 |

*not according to the invention

Within these measurements, alkoxyalkyl imidazoles have an equal efficiency than the additives N-butylbenzimidazole for a dye-sensitized solar cell containing Z907.

As can be shown, the additive 1-(3,3,4,4,4-pentafluorobutyl)-1H-imidazole gives an equal or higher efficiency compared to NBB.

EXAMPLE D

The following electrolyte formulations are synthesized to demonstrate the application of electrolyte formulations according to the invention containing emim TCB in dye sensitized solar cells.

The additive concentration is fixed at 0.25 M for each electrolyte 15 to 20 in addition to the parent mixture of the composition:

I$_2$ 2.5%, mmimI 51.5%, guaSCN 1.0%, emimTCB 45%.

The electrolyte formulations are prepared through mixing of 1,3-dimethylimidazolium iodide (mmimI), 1-methyl-3-ethylimidazolium tetracyanoborate (emimTCB), iodine and guanidiniumthiocyanate. It may be necessary to apply heat up to 60° C. to make the electrolyte formulation homogeneous.

The compounds mmimI, emimI, I$_2$, and emimTCB are commercially available or may be synthesized based on known literature such as Bonhote, P et al. *Inorg. Chem.* 1996, 35, 1168-1178 or such as WO 2004/072089 for the synthesis of organic salts with tetracyanoborate anions.

The following additives are used in the above described electrolyte formulation:

| | |
|---|---|
| Electrolyte 15 | no additive - parent mixture |
| Electrolyte 16 | NBB |
| Electrolyte 17 | 1-(3,3,4,4,4-pentafluorobutyl)-1H-imidazole |
| Electrolyte 18 | 1-(3,3,4,4,4-pentafluorobutyl)-1,2,4-triazole |
| Electrolyte 19 | 1-(3,3,4,4,4-pentafluorobutyl)-1,2,3-triazole |
| Electrolyte 20 | N-(3,3,4,4,4-pentafluorobutyl)-benzimidazole. |

The dye sensitized solar cells are fabricated according to Example A and the measurements were done according to Example A but the dye C106 is used instead of Z907.

Table 4 summarizes the results of the measurements of the above cited electrolyte formulations 15 to 20:

| Electrolyte C106 | $J_{SC}$ [mAcm$^{-2}$] | $V_{OC}$ [V] | FF | η [%] |
|---|---|---|---|---|
| 15 | 11.67 | 0.66 | 0.71 | 5.47 |
| 16 | 11.71 | 0.69 | 0.70 | 5.68 |
| 17 | 11.26 | 0.72 | 0.72 | 5.87 |
| 18 | 11.52 | 0.64 | 0.73 | 5.40 |
| 19 | 11.36 | 0.73 | 0.70 | 5.84 |
| 20 | 11.44 | 0.70 | 0.69 | 5.57 |

As can be shown, the additive 1-(3,3,4,4,4-pentafluorobutyl)-1H-imidazole and 1-(3,3,4,4,4-pentafluorobutyl)-1,2,3-triazole give a higher efficiency compared to NBB.

The invention claimed is:

1. A dye-sensitized solar cell comprising a dye-sensitized electrode and an electrolyte comprising at least one compound of formula I

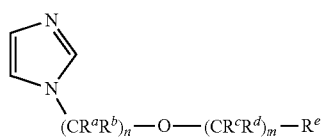

in which
R$^a$, R$^b$, R$^c$, R$^d$ and R$^e$ independently of each other are H, F, Cl or straight-chain or branched alkyl with 1 to 20 C atoms which optionally may be partially or fully fluorinated or chlorinated,
n is 1, 2, 3 or 4,
m is 1, 2, 3 or 4.

2. A dye-sensitized solar cell according to claim 1 wherein the electrolyte comprising at least one compound of formula I is an electrolytic solution.

3. A dye-sensitized solar cell according to claim 1, wherein, in the compound of formula I, R$^a$, R$^b$, R$^c$, R$^d$ and R$^e$ are independently of each other H or F.

4. A dye-sensitized solar cell according to claim 1, wherein, in the compound of formula I, R$^a$, R$^b$, R$^c$, R$^d$ and R$^e$ are H.

5. A dye-sensitized solar cell according to claim 1, wherein the electrolyte further comprises a redox active species.

6. A dye-sensitized solar cell according to claim 5, wherein the redox active species is a combination of iodine and at least one iodide salt.

7. A dye-sensitized solar cell according to claim 1, wherein the electrolyte comprises the at least one compound of formula I in a concentration of from 0.01 to 30 weight % of the electrolyte.

8. A dye-sensitized solar cell according to claim 6, wherein the electrolyte comprises the at least one compound of formula I in a concentration of from 0.01 to 30 weight % of the electrolyte.

9. A dye-sensitized solar cell according to claim 1, wherein the electrolyte further comprises at least one salt compound having a tetracyanoborate anion, a dicyanodifluoroborate anion and/or a fluorotricyanoborate anion.

10. A dye-sensitized solar cell according to claim 5, wherein the redox active species comprises at least one salt having an iodide or a thiocyanate anion and a cation which is an inorganic cation, a guanidinium cation or a protonated amine.

11. A dye-sensitized solar cell according to claim 5, wherein the redox active species comprises at least one salt having an iodide or a thiocyanate anion and a protonated amine cation.

12. A dye-sensitized solar cell according to claim 1, wherein the compound of formula I is 1-(3,3,4,4,4-pentafluorobutyl)-1H-imidazole or 1-(3,3,4,4,4-pentafluorobutyl)-1,2,3-triazole.

13. A dye-sensitized solar cell according to claim 5, wherein the compound of formula I is 1-(3,3,4,4,4-pentafluorobutyl)-1H-imidazole or 1-(3,3,4,4,4-pentafluorobutyl)-1,2,3-triazole.

14. A dye-sensitized solar cell according to claim 1, wherein the compound of formula I is 1-(2'-thioethyl)ethylimidazole.

15. A dye-sensitized solar cell according to claim 5, wherein the compound of formula I is 1-(2'-thioethyl)ethylimidazole.

16. A dye-sensitized solar cell according to claim 1, wherein the dye-sensitized solar cell comprises a photo-electrode, a counter electrode and, between the photo-electrode and the counter-electrode, the electrolyte, and wherein a sensitizing dye is absorbed on the surface of the photo-electrode on the side facing the counter-electrode.

* * * * *